US 6,378,314 B1

(12) United States Patent
Clark

(10) Patent No.: US 6,378,314 B1
(45) Date of Patent: Apr. 30, 2002

(54) CRYOGENIC SYSTEM HAVING UNIQUE STORAGE FRAMES FOR STORING BIO-ORGANIC SPECIMENS

(76) Inventor: Charles J. Clark, 12009 N. Mayfair, Spokane, WA (US) 99218

( * ) Notice: Subject to any disclaimer, the term of this patent is extended or adjusted under 35 U.S.C. 154(b) by 0 days.

(21) Appl. No.: 09/778,199

(22) Filed: Feb. 6, 2001

(51) Int. Cl.$^7$ .................................................. F25B 19/00
(52) U.S. Cl. ............................ 62/51.1; 62/60; 62/457.9
(58) Field of Search ................................ 62/51.1, 457.9, 62/60

(56) References Cited

U.S. PATENT DOCUMENTS 2,260,450 A * 10/1941 Guinane ......................... 62/60
2,964,920 A * 12/1960 Staebler ......................... 62/60
3,875,754 A *  4/1975 Faust et al. .................... 62/64

OTHER PUBLICATIONS

MVE, Inc. Product Brochure, "Cryo–Preservation Equipment", pp. 1–22, 1997.

Custom BioGenic Systems Product Brochure, "Inventory Control Racks", Mar. 1996.

* cited by examiner

*Primary Examiner*—Ronald Capossela
(74) *Attorney, Agent, or Firm*—Wells St. John P.S.

(57) ABSTRACT

A preferred embodiment of a bio-medical cryogenic system 10 is described having a unique canister support frame 100. The frame 100 is elongated when in the upright position having side walls 102 and 104, a top wall 114, a bottom wall 118, a back wall 122 and internal dividers 132 forming a narrow elongated cavity subdivided into canister compartments 136 having a front opening 130. Upright abutment lips 121 and 138 are positioned in the compartments 136 to prevent canisters 50 from being inadvertently dislodged from the compartments 136. Access slots 150 are formed in the back wall 122 and at least one of the side walls 102,104 to enable a laboratory person to insert their finger into the slot and push a canister forward while the other hand is lifting a front portion of the canister above the abutment lip 121 or 138.

6 Claims, 8 Drawing Sheets

US 6,378,314 B1

CRYOGENIC SYSTEM HAVING UNIQUE STORAGE FRAMES FOR STORING BIO-ORGANIC SPECIMENS

TECHNICAL FIELD

This invention relates to cryogenic systems for storing bio-organic specimens for medical and/or medical research purposes and more particular to cryogenic storage vessels having removable storage frames for supporting canisters containing bio-organic specimens.

BACKGROUND OF THE INVENTION

Cryogenic systems have been available for many years for storing bio-organic specimens at sub-zero temperatures for long periods of time. Such systems have become even more important for short and long term preservation of living organisms so vitally important to the biomedical industries.

Often the living organism or bio-specimen is placed in a specimen container or bag, which is in turn placed in a metal storage canister. Several canisters are then placed edgewise one above the other in vertically spaced compartments of a tall thin frame shaving a top lifting handle. After the canisters are loaded into the portable frames, the frames are then lowered into a cryogenic vessel, the interior of which is maintained at an appropriate sub-zero temperature for short or long periods of time. Such cryogenic systems are quite expensive, thus it is advisable to pack as many frames into the cryogenic vessel as reasonably possible. However such close packing makes it rather difficult to remove a single or group of frames without bumping into other frames or the vessel itself.

It is generally necessary, when handling the sub-zero canisters and frames, for the medical or research personnel to use bulky gloves or mittens making it somewhat difficult to load and unload the canisters into and out of the frames. Consequently it is not unusual for one or more of the canisters to be dislodged from the frames as the frames are being inserted or removed from the cryogenic vessel. The dislodged canisters may fall to the bottom of the vessel requiring that a substantial portion of the contents of the vessel be removed in order to retrieve a fallen canister. Such a procedure can be very time consuming and possibly injurious to the specimens and the laboratory personnel.

One of the principle objects of this invention is to provide an unique cryogenic specimen frame that is very cost effective that prevents canisters from being inadvertently dislodged from the frame while enabling a laboratory person to easily remove a canister from a frame, even while wearing low temperature gloves or mittens.

These and other objects and objectives of this invention will become apparent upon reading the following description of a preferred embodiment.

BRIEF DESCRIPTION OF THE DRAWINGS

Preferred embodiments of the invention are described below with reference to the following accompanying drawings.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

Figure 1:
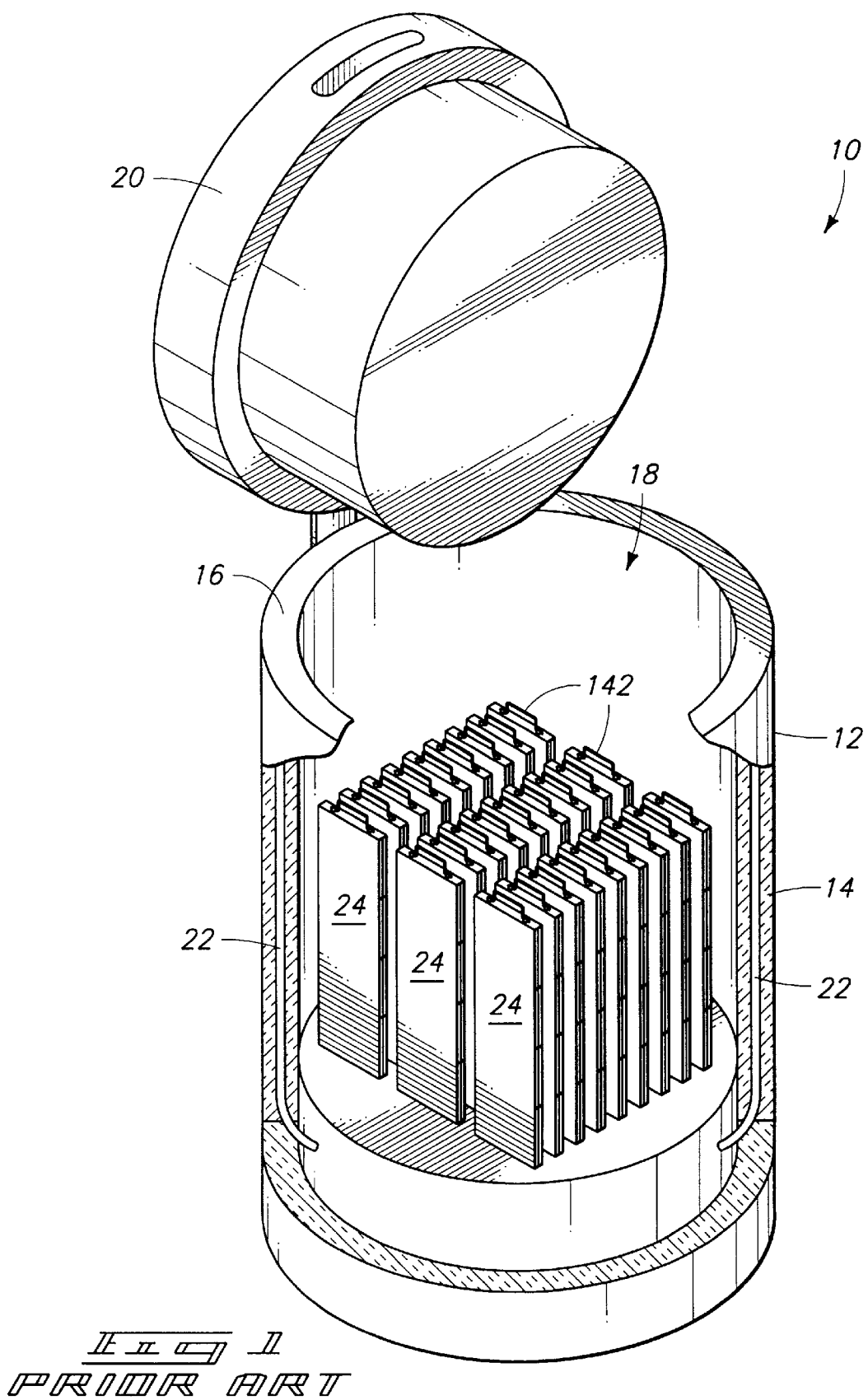
FIG. 1 is an isometric fragmentary view of a cryogenic vessel with a side wall broken away to expose a portion of the vessel interior to show several prior art cryogenic specimen frames mounted therein.

FIG. 1 illustrates a cryogenic system generally designated with the numeral 10 that includes a cryogenic vessel 12 have a side wall 14 and a top wall 16. The top wall 16 has an egress opening 18 which is normally closed by a removable lid or door 20. Normally the vessel 12 has fluid/gas conduit 22 leading to and from the vessel 12 for suppling liquid nitrogen to the interior or walls of the vessel to maintain the interior temperature of the to vessel below zero to preserve bio-organic specimens contained therein.

Figure 2:
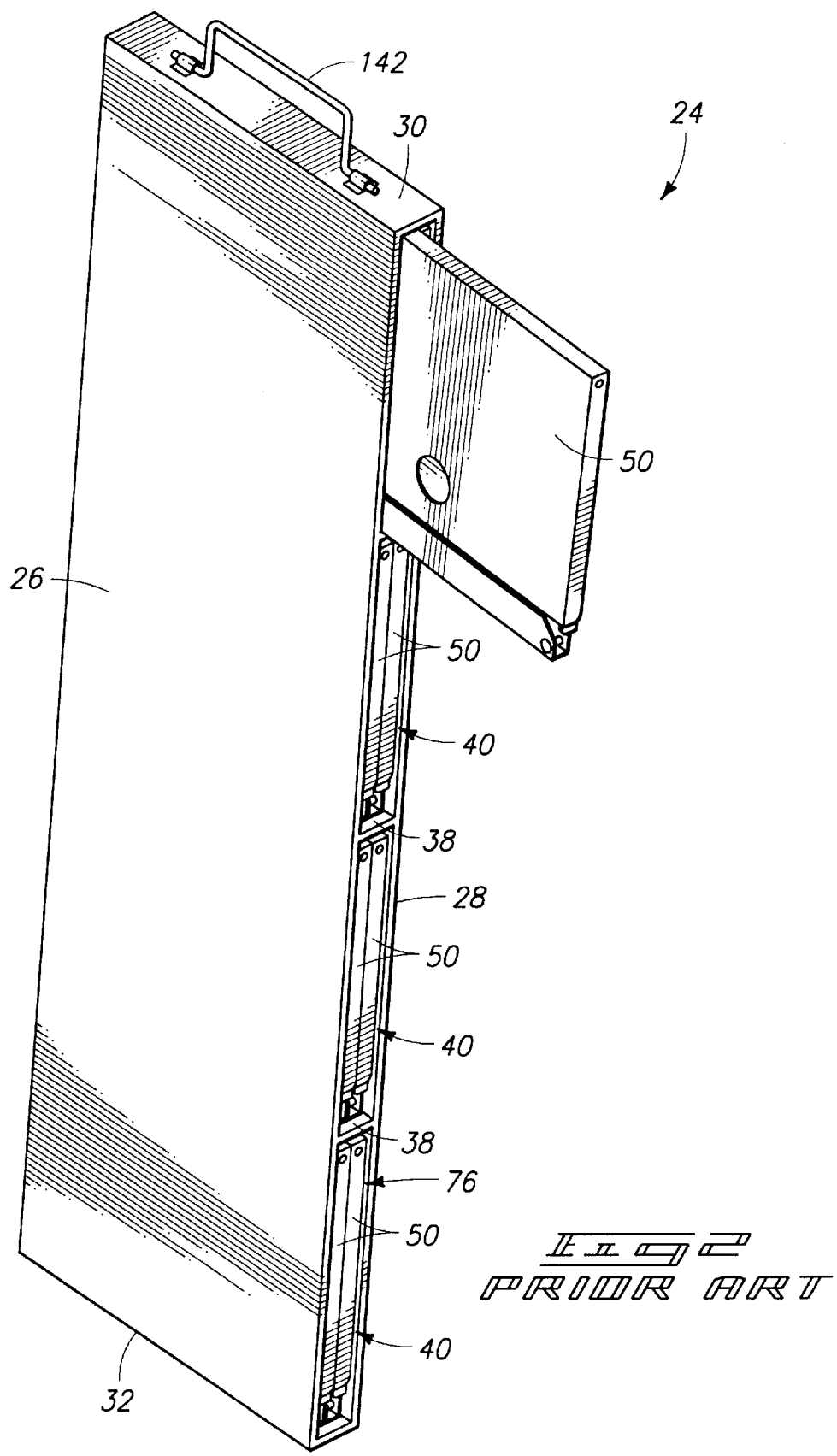
FIG. 2 is an isometric view of a prior art frame with bio-organic specimen canisters mounted therein, in which one of the specimens is shown being partially dislodged.
Figure 3:
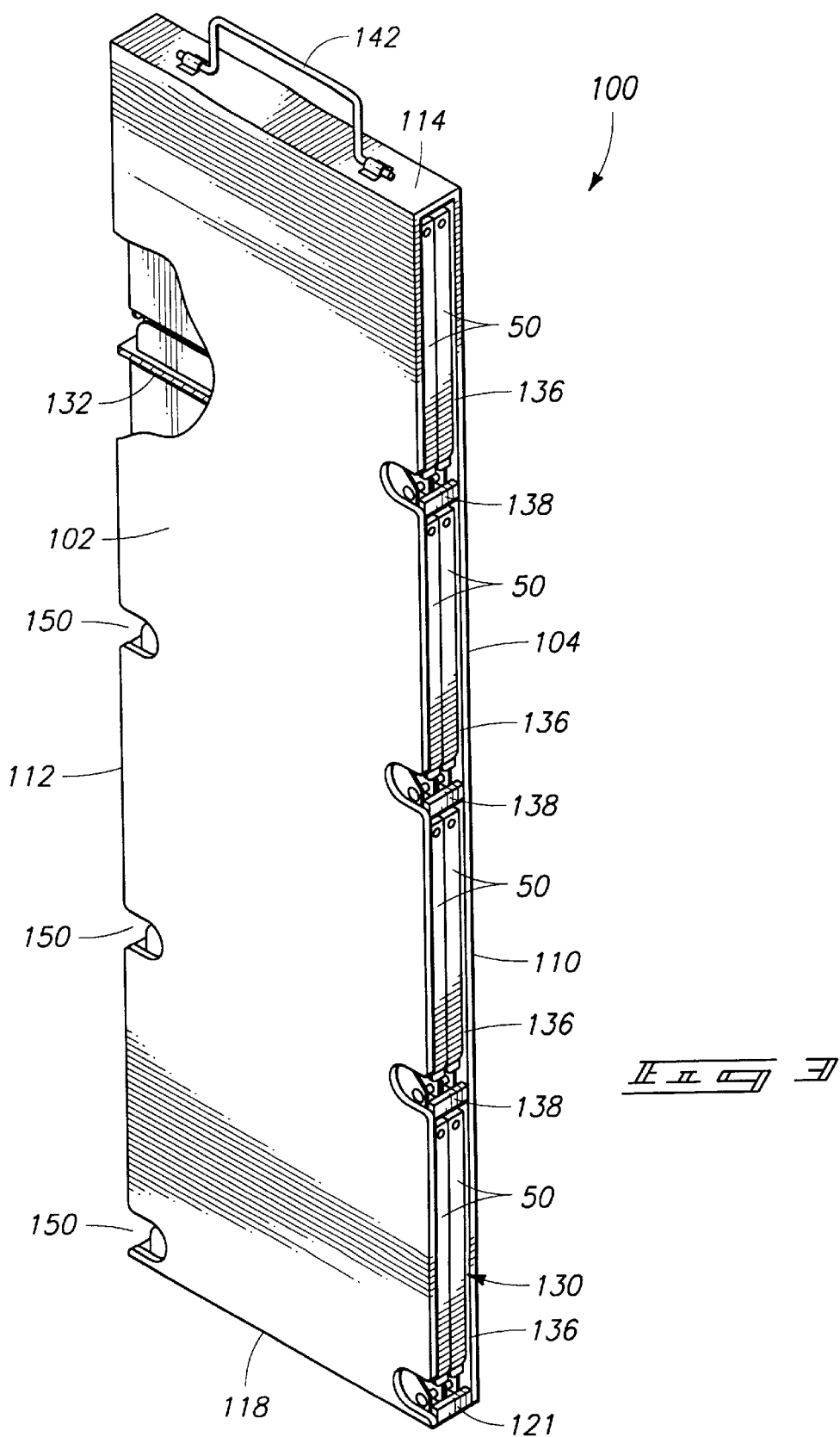
FIG. 3 is an isometric view of a preferred embodiment of the present invention showing an unique cryogenic specimen frame loaded with canisters.

For purposes of illustration, commercially available (prior art) specimen support frames 24 are shown mounted in the vessel 12 in upright orientations. Each frame 24 supports several specimen canisters 50. Each of the specimen frames 24 (FIG. 2) has elongated side walls 26 and 28, top wall 30, back wall (not shown) and bottom wall 32. The frame 24 has an elongated normally vertical front opening. The interior of the frame is subdivided by channel elements 38 into vertically spaced canister compartments 40 for receiving specimen canisters 50. The frame 24 has a handle 42 on the top wall 30 to facilitate the placement and removal of the frame 24 from the interior of the vessel 12.

Figure 4:
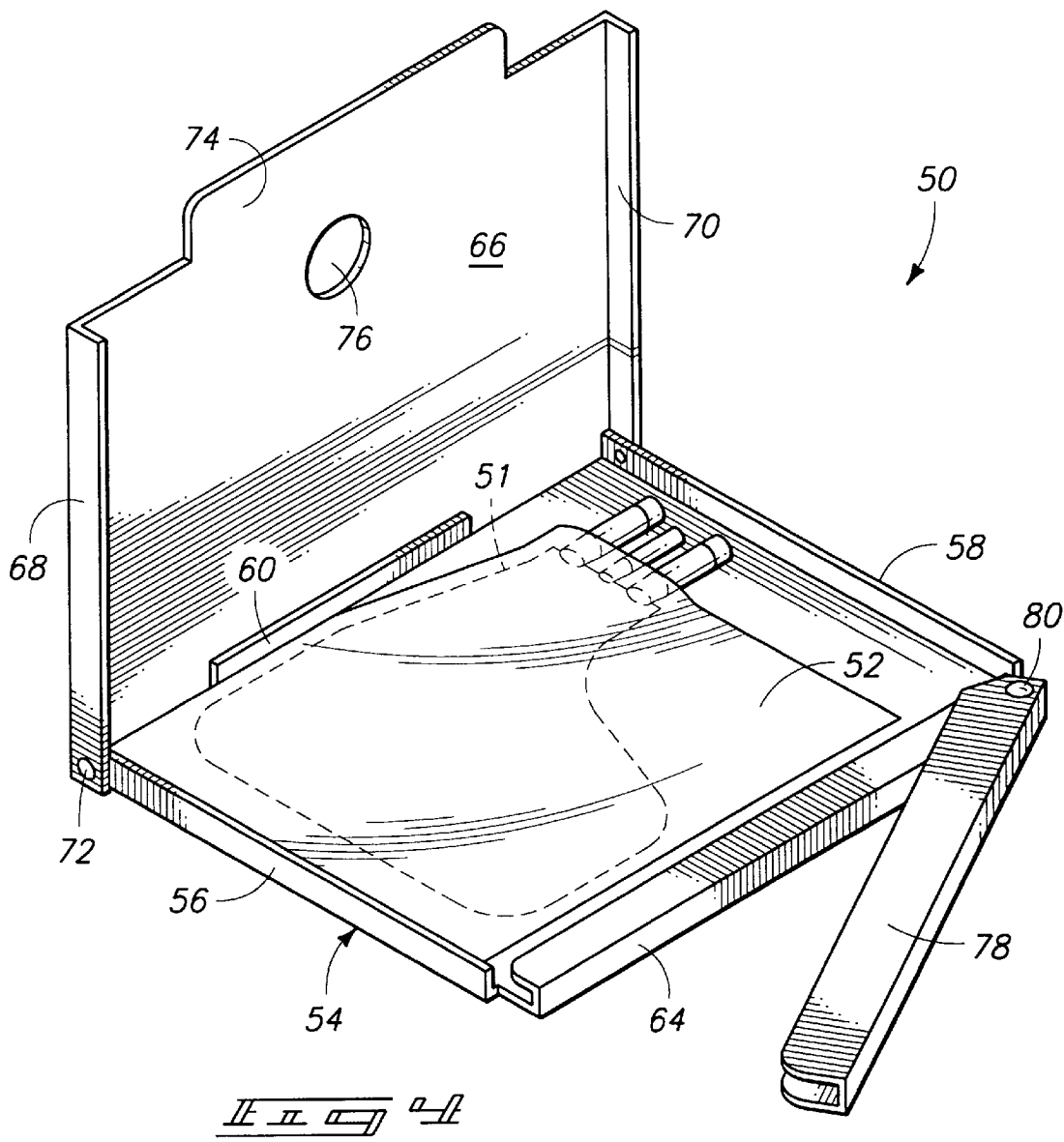
FIG. 4 is an isometric view of preferred embodiment of one of the canister shown in FIG. 3, showing the canister with its lid open with a bio-bag mounted therein containing a bio-organic specimen.
Figure 5:
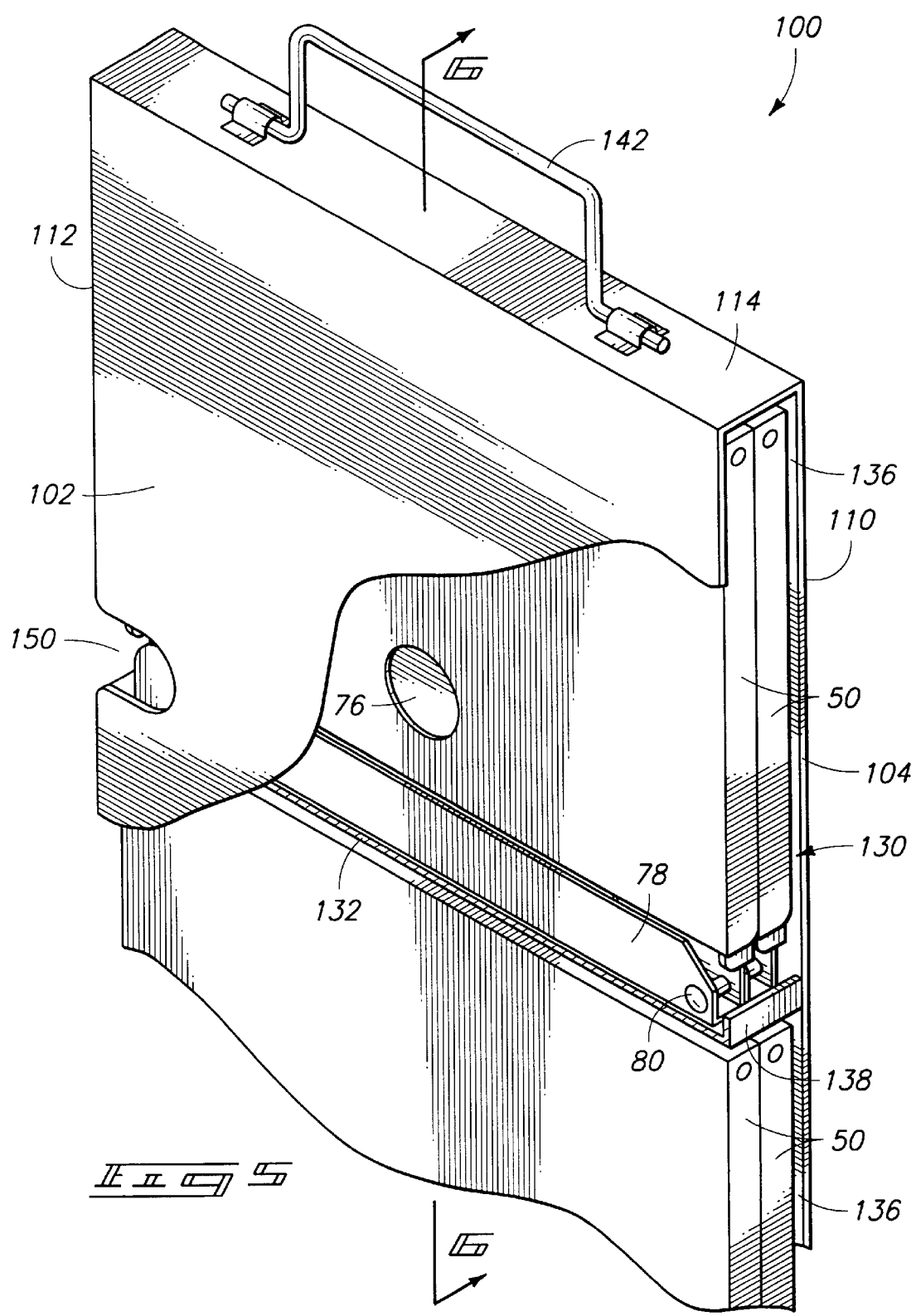
FIG. 5 is an isometric fragmentary view of the frame shown in FIG. 3 showing the components of the frame in more detail to emphasize the simplicity of the present invention.

Each specimen canister 50 is designed to receive, enclose and protect at least one bio-organic specimen 51 (FIG. 4). Frequently the bio-organic specimen 51 is initially placed in a transparent bag or container 52 and then the bag 52 and specimen are placed into the interior of the canister 50.

Each canister 50 has a bottom wall 54, side walls 56 and 58, a back wall 60, a front channel 64 and a top cover or lid 66. The lid 66 has side flanges 68 and 70 that extend downward along side the interior of the side walls 56 and 58 respectively. Pivot rivets 72 interconnect the side flanges 68 and 70 with the side wall 56 and 58 respectively adjacent the back wall 60 to enable the lid 66 to be pivoted about the pivot rivets 72 to open the canister 50 when the lid 66 is pivoted upward and to close the canister 50 when the lid 66 is pivoted downward.

The lid 66 has a lid tongue 74 formed thereon for engaging a top surface of the front channel 64 when the lid 66 is closed. The lid 66 has a finger aperture 76 formed therein to facilitate retrieval of the contained specimen.

The canister 50 further contains a "U" shaped locking channel 78 that fits over the front channel 64 to hold the lid tongue 74 against the channel 64 to lock the lid 66 in the closed position when the canister 50 is mounted in a frame 24. The channel 78 is pivotally attached to the channel 64 by a pivot rivet 80 adjacent one of the side walls 56 and 58.

A preferred embodiment of a greatly improved canister support frame 100 which is the subject of this invention is illustrated in more detail in FIGS. 3 and 5–7. The canister support frame 100 has elongated side walls 102 and 104 that are preferably formed of aluminum sheet metal that extend from top ends to bottom ends and extend from front edges 110 to rear edges 112. The canister support frame 100 has a narrow top wall 114 interconnecting the top ends of the side walls 102 and 104.

The canister support frame 100 has a narrow bottom wall 118. The bottom wall 118 further includes an upward extending abutment or lip 121 adjacent the front edge 110 of the side walls 102 and 104.

Figure 8:
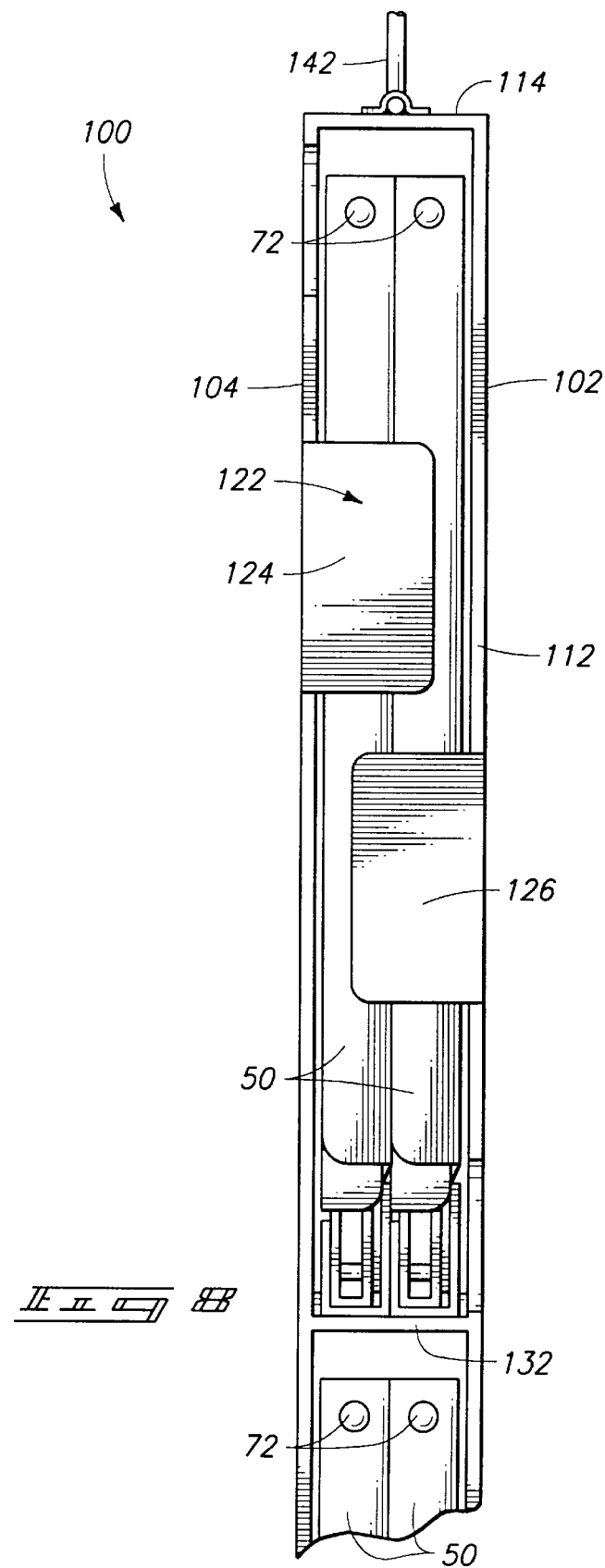
FIG. 8 is a fragmentary rear view of the frame shown in FIG. 5 illustrating a back wall of the frame to prevent the enclosed canister from being removed from the rear.

The frame 100 has a back wall 122 (FIG. 8) that is formed by overlapping tabs 124 and 126 that are formed integrally with the side walls 102 and 104 respectively and are bent inwardly at right angles. The side walls 102 and 104, the top wall 114, the bottom wall 118 and the back wall 122 form an enclosure about a long narrow, normally upright frame cavity having a narrow elongated front opening 130 extending along the front edges 110 of the side walls 102 and 104.

The specimen support frame 100 has a plurality of horizontal dividers 132 extending between the side walls 102 and 104 to divide the frame cavity into vertically spaced canister compartments 136 for receiving and supporting two side-by-side canisters 50 in each compartment 136. Preferably the dividers 132 are spaced equal distance from each other to form compartments 136 of approximately equal size.

The specimen support frame 100 has abutments means adjacent the front opening of each compartment 136 to prevent the contained canisters 50 from be inadvertently dislodged from the compartment 136. Preferably the abutment means is in the form of lips 138 formed on the dividers 32 adjacent the front edges 110 of the side walls 102 and 104 and the lip 121 that extend upward into the front opening 130 preventing the canisters 50 from sliding out of the compartments 136 as the frame(s) is being lifted into or out of the cryogenic vessel (see FIG. 6). Each of the specimen support frames 100 is provided with a handle 142 that is attached to the top wall 114 to facilitate upright handling of the frame 100 and it contained canisters 50.

Figure 7:
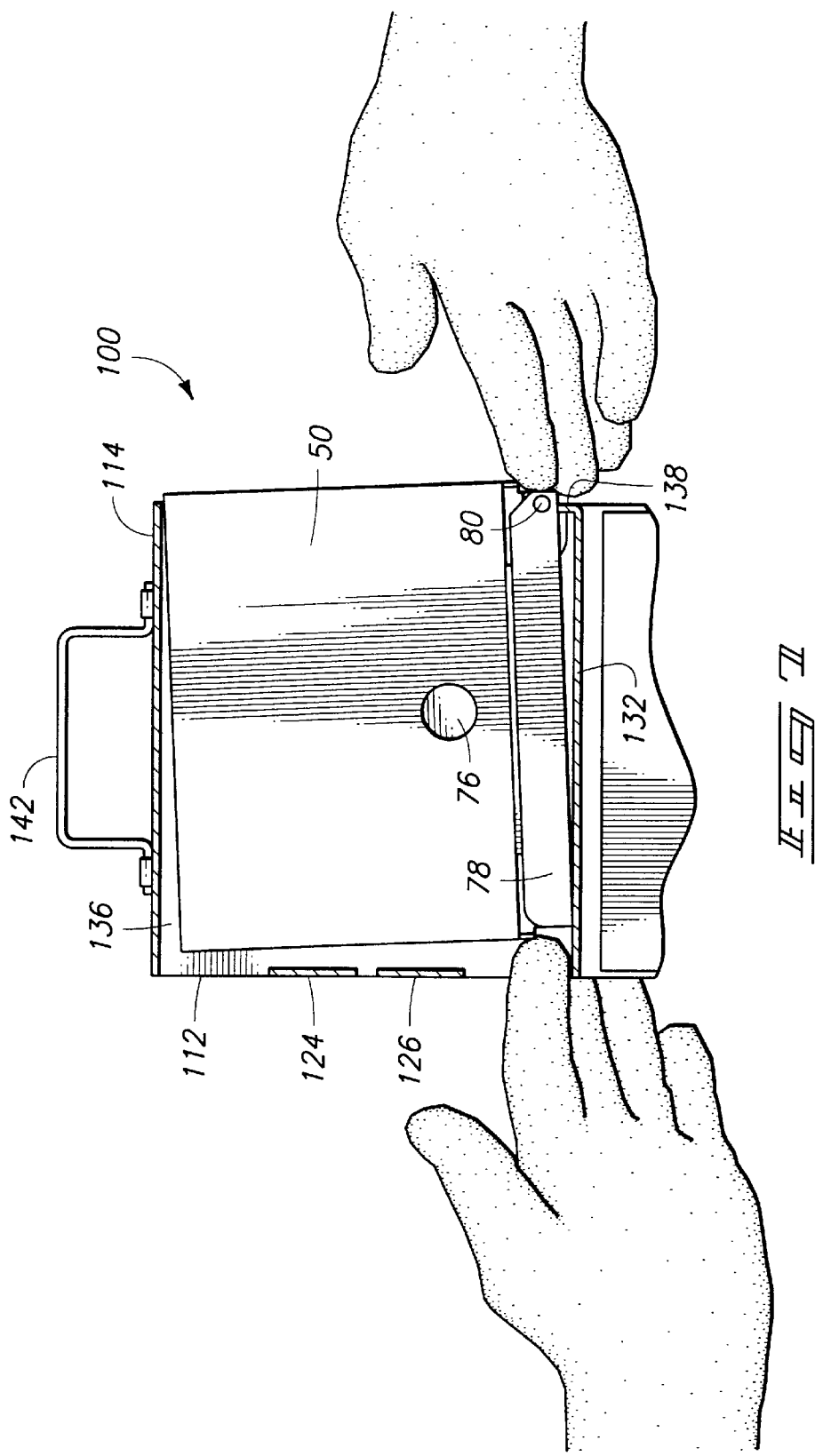
FIG. 7 is a fragmentary vertical cross-sectional view similar to FIG. 6, except showing the fingers of a laboratory person partially removing the canister from the frame.

The canister support frame 100 has access slots or apertures 150 formed in at least one of the side walls 102, 104 adjacent the back wall 122 to enable a laboratory person to insert a finger or other object into the slot 150 and exert a pushing force against a rear portion of a contained canister 50 as depicted in FIG. 7 and to push the canister 50 forward once the front portion of the canister is lifted about the compartment lip 121, 138.

Figure 6:
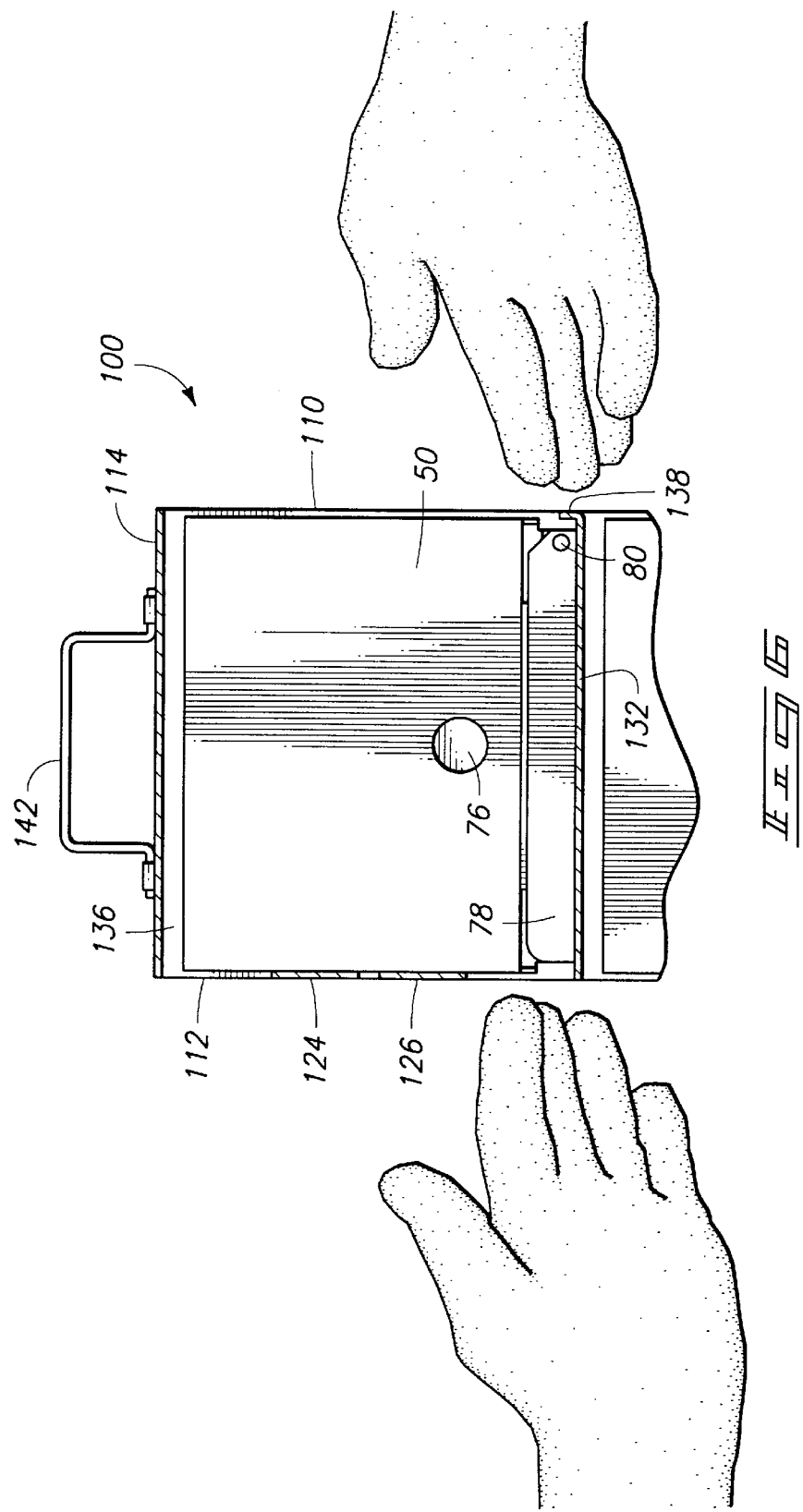
FIG. 6 is a fragmentary vertical cross-sectional view taken along line 6—6 in FIG. 5 with a portion of a side wall removed to show a compartment lip holding a canister in the frame prior to use of hands to remove the canister from the frame.

FIGS. 6 and 7 illustrates a process for removing a canister 50 from a compartment 136. While using both hands together, the laboratory person engages a front portion of canister with one hand, in this case the right hand, and then inserts either their finger or tool into the access slots 150 to exert a pushing force on a rear portion of the canister. The laboratory person then moves or lifts the front portion of the canister above and clear of the associated lip 121 or 138 while continuing to push with the other hand causing the front portion of the canister to project from the front opening 130. The laboratory person then is able to easily grip the projecting canister with their right hand and pull the canister 50 free from the frame.

Thus while the canister support frame 100 is being held by the handle 142 and moved into or out of the cryogenic vessel 12, the contained canisters 50 are held in their respective compartments and prevented from sliding out, even though the frame 100 may be bumped or engage by a foreign object. It is only when the laboratory person uses both hands in concert with each other that a canister may be easily removed from its compartment 136.

It can be easily appreciated that the canister support frame 100 is very cost effective and efficient in providing a very sturdy structure for supporting and preventing unintended canister 50 dislodgement while the frame 100 is being loaded into or removed from the cryogenic vessel 12 and for enabling efficient, intended removal of a canister 50 from the frame 100.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. In a cryogenic system for storing bio-organic specimens at sub-zero temperatures in a cryogenic vessel, a cryogenic storage specimen frame for receiving and supporting one or more bio-organic specimen canisters, comprising:

elongated, normally upright, side walls extending between bottom ends and top ends;

a narrow top wall extending between the top ends of the side walls; said top wall having a handle thereon to enable the frame to be carried upright;

a narrow bottom wall extending between the bottom ends of the side walls;

a narrow back wall extending between the side walls to partially enclose the frame defining an elongated narrow, normally upright, frame cavity having an elongated narrow front opening;

at least one frame divider extending between the side walls spaced from the top and bottom walls dividing the frame cavity into more than one normally vertically spaced compartments for receiving and supporting canisters therein; and abutment means projecting into each compartment adjacent the front opening for preventing a canister from inadvertently being dislodged from the frame.

2. In the cryogenic system as defined in claim 1 wherein at least one of the side walls has finger slots formed therein to enable laboratory personnel to lift the canister above the abutment means and move the canister at least partially through the front opening.

3. In the cryogenic system as defined in claim 1 wherein the abutment means includes a lip formed on the dividers adjacent the front opening to prevent the canisters from being inadvertently dislodged from the frame.

4. In the cryogenic system as defined in claim 2 wherein the slots are formed in the back wall and extend partially toward the front opening providing access to a rear portion of the canister to enable the laboratory person to lift a canister bottom edge above abutment means with one hand and then push a rear edge of the canister forward with the other hand to move the canister at least partially outward through the front opening.

5. In the cryogenic system as defined in claim 1 wherein the back wail is formed by tabs formed integrally with the side walls that extend at substantially right angles from rear edges of the side walls.

6. In the cryogenic system as defined in claim 1 wherein the top wall is formed integrally with one side wall and the bottom wall is formed integrally with the other side wall.

* * * * *

UNITED STATES PATENT AND TRADEMARK OFFICE
CERTIFICATE OF CORRECTION

PATENT NO.  : 6,378,314 B1
DATED       : April 30, 2002
INVENTOR(S) : Charles J. Clark It is certified that error appears in the above-identified patent and that said Letters Patent is hereby corrected as shown below:

Column 2,
Line 35, replace "interior temperature of the to vessel below zero" with -- interior temperature of the vessel below zero --

Column 3,
Line 41, replace "32 adjacent the front edges 110 of the" with -- 132 adjacent the front edges 110 of the --

Signed and Sealed this

Eleventh Day of February, 2003

JAMES E. ROGAN
*Director of the United States Patent and Trademark Office*